Figure 4:
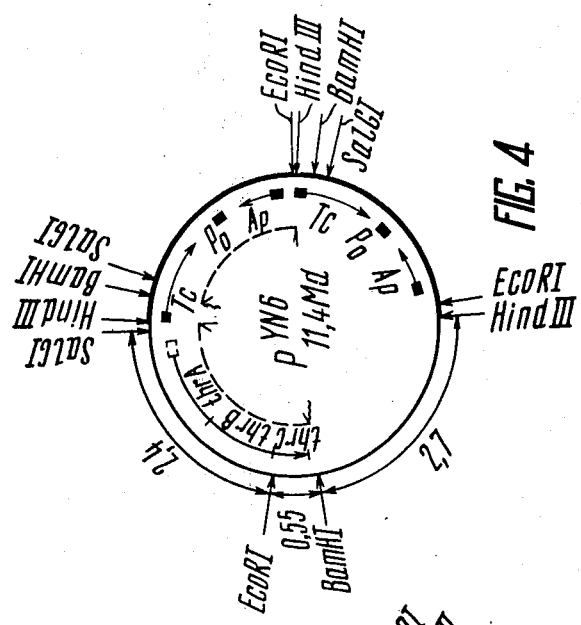

United States Patent [19]

Debabov et al.

[11] 4,278,765

[45] Jul. 14, 1981

[54] METHOD FOR PREPARING STRAINS WHICH PRODUCE AMINOACIDS

[76] Inventors: Vladimir G. Debabov, ulitsa Miklukho-Maklaya, 43, kv. 57; Jury I. Kozlov, Mikroraion 2, korpus 3, kv. 178; Nelli I. Zhdanova, Leningradskoe shosse, 112, korpus 3, kv. 748; Evgeny M. Khurges, ulitsa Tikhvinskaya, 1/13, kv. 16; Nikolai K. Yankovsky, ulitsa Verkhnaya Radischevskaya, 13/15, kv. 59; Mikhail N. Rozinov, 3 Frunzenskaya ulitsa, 6, kv. 161; Rustem S. Shakulov, ulitsa Krasnogo Mayaka, 14, korpus 2, kv. 106; Boris A. Rebentish, ulitsa 11 Sokolnicheskaya, 12, kv. 16; Vitaly A. Livshits, ulitsa Kirovogradskaya, 24, korpus 3, kv. 8; Mikhail M. Gusyatiner, Suschevsky val, 22, kv. 28; Sergei V. Mashko, ulitsa Nizhnaya Pervomaiskaya, 5, kv. 16; Vera N. Moshentseva, ulitsa Krupskoi, 5, kv. 67; Ljudmila F. Kozyreva, 4 Novopodmoskovny pereulok, 4, kv. 80; Raisa A. Arsatiants, Mikroraion 2, korpus 3, kv. 178, all of Moscow, U.S.S.R.

[21] Appl. No.: 52,744

[22] Filed: Jun. 28, 1979

[30] Foreign Application Priority Data

Jun. 30, 1978 [SU] U.S.S.R. ................................ 2639616

[51] Int. Cl.$^3$ ................................................ C12N 15/00
[52] U.S. Cl. ..................................... 435/172; 435/115; 435/317; 435/820
[58] Field of Search ........................................... 435/172

[56] References Cited

PUBLICATIONS

Sinsheimer, Ann. Rev. Biochem 46, 415–438, 1977.
Itokura et al., Science vol. 98, pp. 1056–1063.

*Primary Examiner*—Alvin E. Tanenholtz
*Attorney, Agent, or Firm*—Lackenbach, Lilling & Siegel

[57] ABSTRACT

A method for constructing strains which produce aminoacids comprising combining of a DNA chromosome fragment of a donor microorganism containing genes controlling the synthesis of a selected aminoacid and having a mutation destroying the negative regulation of the synthesis of this aminoacid with a vector DNA molecule to form a hybrid DNA molecule. Use is made of a vector DNA molecule capable of providing amplification of the hybrid DNA molecule. The resulting hybrid DNA molecule is used for transforming cells of the recipient strain having the mutation blocking the synthesis of the selected aminoacid in this strain and the mutation partly blocking the related step of metabolism of this aminoacid to yield the strain capable of increased productivity of the selected aminoacid.

4 Claims, 5 Drawing Figures

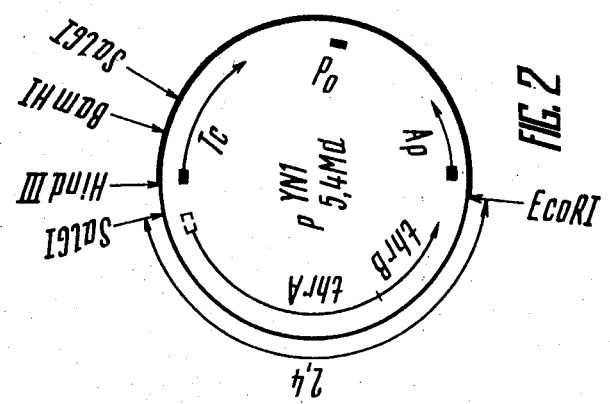
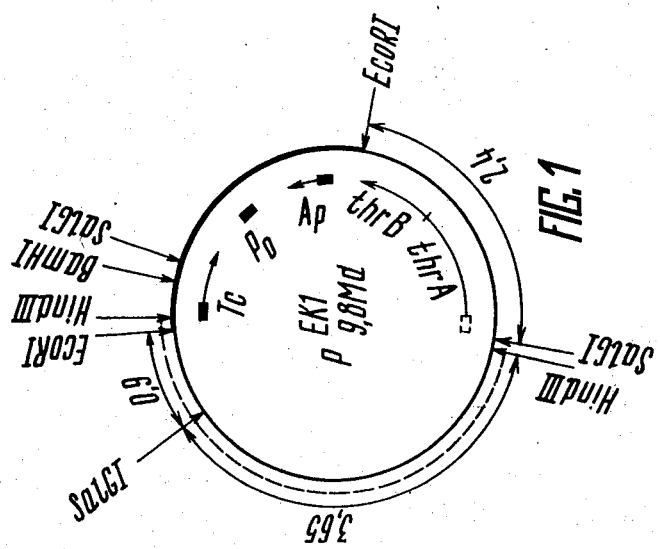

METHOD FOR PREPARING STRAINS WHICH PRODUCE AMINOACIDS

The present invention relates to the microbiological industry and, more specifically, it relates to a method for preparing strains which produce aminoacids.

Aminoacids produced by microorganisms find extensive use as feedstuff and food additives in the agriculture and food industry, as components of various nutrient mixtures for medical purposes and as reagents in the chemical and pharmaceutical industries.

In the text of the description of the present invention, the following expressions and terms are used.

The term DNA means deoxyribonucleic acid.

Plasmids are genetic elements reproducing in bacterial cells irrespective of chromosome.

Replication means reproduction of genetic material.

Transformation means transfer of genetic bacterial material to a bacterial cell by means of isolated DNA.

Transfection means transfer of genetic material of a phage to a bacterial cell by means of isolated DNA.

The term vector molecules denotes DNA molecules of plasmids and phages ensuring transfer of a foreign genetic material to a cell and its autonomous replication.

The term recombinant (hybrid) molecules of DNA denotes DNA molecules produced in vitro as a result of ligation, into one molecule, of different DNA molecules one of which is a vector molecule.

The term clone means genetically uniform progeny of one cell.

The term cloning of genes (molecular cloning) denotes preparation of clones of bacteria containing said genes on a hybrid plasmid.

Amplification means increasing the number of genes in a cell.

Conjugation means transfer of genetic material upon contact of bacterial cells.

Transduction means transfer of genetic material by means of a bacteriophage.

The term auxotrophic strains means mutant organisms incapable of synthesizing aminoacids or other growth factors and growing only in the presence of these factors in a nutrient medium.

The term protrophic strains means wild-type organisms capable of growing on minimal glucose-salt nutrient media.

Operon means a jointly controlled group of genes generally monitoring the synthesis of a single product, e.g. aminoacid.

The term catabolism means the process of converting complex compounds to simple ones.

The term repression means switch off transcription of genes or operons resulting in the termination of synthesis of enzymes.

The term repressor denotes a regulating protein which stops the functioning of genes in combination with repression cofactors (usually final products of the biosynthesis or their derivatives).

The term specific endonuclease (restrictase) means an enzyme cleaving a double stranded DNA molecule to fragments in sites with a specific sequence of bases.

The term polynucleotide ligase means the enzyme joining DNA fragments produced by means of endonucleases.

The term replicon means a genetic material capable of replication.

The term phenotype means manifestation of genetic features under given external conditions.

Known in the art are methods for preparing strains which produce aminoacids such as L-lysine, L-threonine, L-isoleucine and the like by using various mutagens (UV, ionisation radiation, chemical mutagens). The resulting mutant strains of microorganisms have specific genetically preconditioned defects in regulating metabolism and, due to such defects, they evolve into the nutrient medium, or produce, specific aminoacids. The required mutant strains of microorganisms are produced by conventional methods based on the particular nutritive demand of a mutant (auxotrophy) or on resistance of a mutant with respect to one or another structural analogues of an aminoacid inhibiting the growth of the parental strain (cf. British Pat. Nos. 1,258,380; 1,186,988; 1,316,888; Japanese Pat. No. 51-6237).

Known in the art is also a method for preparing mutants which produce aminoacids on the basis of simultaneous resistance against an antimetabolite (antibiotic or aminoacid analogue) and coinhibitor (a particular aminoacid); (cf. U.S. Pat. No. 3,756,916).

In all the above-mentioned cases, mutant strains capable of producing aminoacids are prepared by a single or step-by-step induction of mutations in a genetic structure (genome) of the parental strain evolving no amino acid.

Hitherto unknown are strains characterized by increasing production of an aminoacid due to increasing the dose of genes necessary for its biosynthesis or as a result of introducing of a additional genetic material into a cell. Not known are strains to increase production of an aminoacid due to the application of genetic engineering methods, i.e. methods of operation with recombinant molecules of DNA.

The present practice of genetic studies uses methods of in vitro preparation of hybrid DNA molecules capable of autonomous replication and amplification and introduction of these molecules into a recipient strain, by means of transformation or transfection. As vector molecules, use is made of plasmid DNA or DNA of temperate bacteriophages. These methods are described in detail in the following publications:

1. Cohen S. N., Chang A. C. Y., Boyer H. W. and Helling R. B. Proc. Nat. Acad. Sci. U.S.A., 70, 3240, 1973.
2. Green P. J., Betlach M. C., Boyer H. W., Goodman H. N. Methods in Molecular Biology, 7, 87, 1974.
3. Tanaka T., Weisblum B. J. Bacteriol., 121, 354, 1975.
4. Clarke L., Carbon J. Proc. Acad. Sci. U.S.A., 72, 4361, 1975.
5. Bolivar F., Rodrigues R. L., Green P. J., Betlach M. C., Heyneker H. L., Boyer H. W. Gene, 2, 95, 1977.
6. Kozlov J. I., Kalinina N. A., Gening L. V., Rebentish B. A., Strongin A. J., Bogush V. G., Debabov V. G. Molec. Gen. Genetics, 150, 211, 1977.

Certain practical aspects of applying of genetic engineering methods are revealed in the method for preparing the strains Pseudomonas involving degradation of complex organic compounds (petroleum hydrocarbons) (cf. U.S. Pat. No. 3,923,603) This patent teaches in vivo preparation of hybrid molecules by way of intracellular recombination.

However, methods for preparing strains producing aminoacids with the use of genetic engineering techniques are hitherto unknown.

It is an object of the present invention to use, genetic engineering techniques, to prepare strains which produce aminoacids possessing enhanced capability of producing aminoacids without additional growth factors.

This object is accomplished by a method for preparing strains which produce aminoacids, wherein according to the present invention, a chromosone DNA fragment of a donor microorganism containing genes controlling the synthesis of a selected aminoacid and having a mutation breaking the negative regulation of the synthesis of this aminoacid, is combined with a vector molecule of DNA with the formation of a hybride DNA molecule. In so doing, use is made of a vector molecule of DNA capable of ensuring amplification of a hybrid DNA molecule. The resulting hybrid molecule of DNA is used for transforming cells of a recipient strain having a mutation blocking the synthesis of the selected aminoacid in this strain and a mutation partly blocking the related step of metabolism of this aminoacid to give a strain possessing increased productivity with regard to the selected aminoacid.

To remove the ballast genetic material and to increase stability of a hybrid plasmid, as well as to increase the number of its copies in a cell, it is advisable that the resulting hybrid molecule of DNA be treated, prior to transformation of cells of the recipient strain, with specific endonucleases to ensure cleaving hybrid DNA molecule at definite sites, followed by joining the required DNA fragments with polynucleotide ligase.

In accordance with the present invention, the method for preparing a strain which produces an aminoacid such as L-threonine, resides in that a fragment of DNA chromosome of a donor strain E. coli VNIIGenetika MG442 containing genes of threonine operon wherein enzyme products of the gene thrA are stable to inhibition with threonine as a result of mutation, said fragment being produced by means of endonuclease Hind III, is combined with a vector molecule of DNA (as such vector molecule use is made of plasmid pBR322) to form a hybrid plasmid having molecular weight of 11.4 Megadalton (Md) and consisting of two copies of the plasmid pBR322 and said chromosome DNA fragment of the donor strain. This ensures resistance of cells to penicillin and tetracycline and may be contained in cells in the stage of logarithmic growth in an amount of about 10 copies. The resulting hybrid plasmid is used to transform cells of the recipient strain E. coli VL334 having mutations blocking the synthesis of L-threonine and L-isoleucine. This blocking is partial with respect to L-isoleucine and may be compensated by an increased content of threonine in a cell. These mutations ensure a selective advantage to the cells containing the hybrid plasmid over the cells which lost the plasmid during culturing. The strain produced is E. coli VNIIGenetika VL334 (pYN6) which produces L-threonine and is deposited in the Central Museum of Industrial Microorganisms of the All-Union Research Institute of Industrial Microorganisms identified by the registration number CMIM B-1649. The term VNIIGenetika is a contraction of the title of the All-Union Research Institute of Genetics and Selection of Industrial Microorganisms (Vsesojouzny Nauchno-Issledovatelsky Institut Genetiki i Selektsii Promyshlennykh Microorganismov). The parent strains of VNIIGenetika MG442 and VNIIGenetika VL334 are also desposited in the aforesaid Central Museum and are identified by the registration numbers CMIM B-1628 and CMIM B-1641, respectively.

Another embodiment of the method for preparing a strain which produces the aminoacid L-threonine resides in that a chromosome DNA fragment of the donor strain E. coli VNIIGenetika MG442 prepared by means of the endonuclease Hind III which contains genes of threonine operon with enzyme-products of the gene thrA, becomes resistant, as a result of mutation, to inhibition by threonine, and is combined with a vector molecule of DNA. A the vector molecule, use is made of the plasmid pBR322 with the formation of a hybrid plasmid having molecular weight of 11.4 Md and containing 2 copies of the plasmid pBR322 and said chromosome DNA fragment of the donor strain. The resulting hybrid plasmid is treated with specific endonucleases Hind III and Bam HI and the thus-produced fragments are joined by polynucleotide ligase. The resulting hybrid plasmid has a molecular weight of 5.7 Md, and consists of one molecule of plasmid pBR322 and said chromosome DNA fragment of the donor strain. It ensures resistance of cells against penicillin and may be contained in cells in the stage of logarithmic growth in an amount of about 20 copies. This resulting hybrid plasmid is used to transform cells of the recipient strain E. coli VL 334 having mutations blocking the synthesis of L-threonine and L-isoleucine. The blocking of L-isoleucine is partial and may be compensated by an increased content of threonine in a cell. These mutations ensure a selective advantage to cells containing the hybrid plasmid during the process of cultivating, and the strain E. coli VNIIGenetika VL334 (pYN7) is prepared which produces L-threonine. This strain is deposited in the Central Museum of Industrial Microorganisms of the All-Union Research Institute of Genetics and Selection of industrial microorganisms under the registration number CMIM B-1684.

The method according to the present invention is effected in the following manner.

To prepare a strain producing a particular aminoacid, a donor strain of a given microorganism is selected along with a chromosome fragment of DNA which contains genes controlling the synthesis of the selected aminoacid. The donor strain is characterized by the presence of said genes to be cloned, or in the regulation region adjacent to said genes, of mutations which break the negative regulation of the synthesis of the required aminoacid. These mutations are in the genes to be cloned, or in the regulatory region adjacent to said genes. These mutations increase the synthesis of the needed aminoacid with the donor strain as compared to the wild-type strain and may be obtained by conventional methods. A vector molecule of DNA, for example, plasmid is selected which ensures replication of the foreign genetic material inserted therein and defines one or more selected features such as resistance to antibiotics. To prepare hybrid molecules, i.e. to combine a chromosome DNA fragment of the donor strain with the vector DNA molecule, they are cleaved into individual fragments by means of a specific endonuclease or otherwise, whereafter the resulting mixture is treated with polynucleotide ligase joining the fragments in a random manner. The thus-prepared mixture is employed to effect a genetic transformation of bacteria, whereupon selection of hybrid plasmids with a fragment of the donor chromosome is effected, said fragment bearing the genes monitoring the synthesis of the required aminoacid. As the recipient agent for the transformation, use is made of a bacterial strain with at least one gene thereof being damaged among those controlling the synthesis of a given aminoacid and which, consequently, is auxotrophic with respect to the required aminoacid. After said transformation the prototrophic transformants are chosen which simultaneously bear the selective features defined by the vector plasmid. These transformants may constitute several phenotypic classes. Hybrid plasmides are isolated from the transformants of every phenotypic class by conventional methods. These hybrid plasmids may carry fragments of DNA chromosome of the donor strain of a different size and contain different number of copies of the vector molecule per cell. The isolated hybrid plasmids are tested for the presence of the chromosome fragment of the donor strain therein, said fragment containing genes monitoring the synthesis of the given aminoacid. To this end, hybrid plasmids are used to transform auxotrophic strains having mutations with respect to each of the genes being cloned. Restoring of prototrophy of transformants in this case indicates the presence of a corresponding gene in the composition of the hybrid plasmide. For further work in constructing the strain producing an aminoacid use is made of hybrid plasmids containing all the selected genes controlling the synthesis of the given aminoacid. In this case, if the isolated plasmids do not contain all the required genes, the above-mentioned operations are repeated by modifying the fragmentation of DNA, e.g. by using another specific endonuclease.

To eliminate the ballast genetic material and improve resistance of the hybrid plasmide and to increase the number of its copies in a cell, the resulting hybrid plasmid should be preferably treated, prior to the following transformation of cells of the recipient strain, with specific endonucleases ensuring splitting thereof in predetermined sites of a molecule, followed by joining the required fragments by polynucleotide ligase.

The thus-prepared hybrid plasmid containing all the selected genes controlling the synthesis of this aminoacid in the given microorganism is employed for genetic transformation of cells of the recipient strain which, after transformation, are capable of ensuring an increased level of synthesis of the predetermined aminoacid. The recipient strain has a mutation blocking the synthesis of the given aminoacid in this strain which makes it possible to easily select transformants bearing the hybrid plasmid with genes monitoring the synthesis of the selected aminoacid. Furthermore, the recipient strain should carry the mutation partly blocking the related step of metabolism of the selected aminoacid. The partial blocking of the related, e.g. subsequent, step of metabolism of the predetermined aminoacid should cause demand in a high concentration of this aminoacid for the synthesis of the metabolite with its precursor being the selected aminoacid. Owing thereto, the recipient cells with hybrid plasmids capable of ensuring the synthesis of a considerable amount of the selected aminoacid have a selective advantage over the plasmidless versions, since they are capable of being grown on a medium without the selected aminoacid and metabolite in respect whereof it is the precursor. It is also advisable that the recipient strain have a mutation breaking the repression of corresponding genes and mutations blocking catabolism and conversions of the predetermined aminoacid. The strains prepared by the method according to the present invention are used for the production of various aminoacids, for example threonine, by way of fermentation on a nutrient medium containing assimilable sources of carbon, mineral nitrogen, mineral salts and ensuring predominant development of the population of cells bearing the hybrid plasmid.

We have carried out a series of experiments on cloning genes of threonine operon in cells of *E. coli* K12; the results of these experiments justify correctness of the method according to the present invention.

The experiments have been performed in the following manner. As the donor strain use is made of the strain *E. coli* W3350 bearing threonine operon of the wild type; as the vector molecule of DNA, use is made of plasmid pBR322. Using restrictional endonuclease Ecc RI for the preparation of DNA fragments, the hybrid plasmid pEKI is obtained. The subsequent treatment of the plasmid pEKI with endonuclease Hind III and polynucleotide ligase results in the creation of the plasmid pYNI which differs from the plasmid pEKI in that it does not carry the fragment of chromosome between two sites of endonuclease Hind III splitting. The plasmids pEKI and pYNI contain only two of the three genes of the threonine operon, i.e. genes thrA and thrB as it is schematically shown in FIGS. 1 and 2.

FIG. 1 shows a restrictional chart of the plasmid pEK1 wherein the thick solid arc denotes the region of the vector plasmid pBR322, while the thin arc shows the cloned fragment of chromosome DNA. The dotted arc indicates the region of the plasmid eliminated upon the construction of the plasmid pYNl. The arrows show the sites of splitting the plasmid with different endonucleases, while figures between the arrows show the distance expressed in Megadaltons. Black rectangles with arrows represent promotor and structural portions, respectively, of genes of stability to tetracycline (Tc), penicillin (Ap), genes of replication region ($P_o$) and the threonine operon.

FIG. 2 shows the restrictional map of the plasmid pYNl. The reference characters are the same as in FIG. 1.

Transformation of the strain *E. coli* C600 with the resulting hybrid plasmid has not given any noticeable increase in the synthesis of threonine by the cells.

Figure 3:
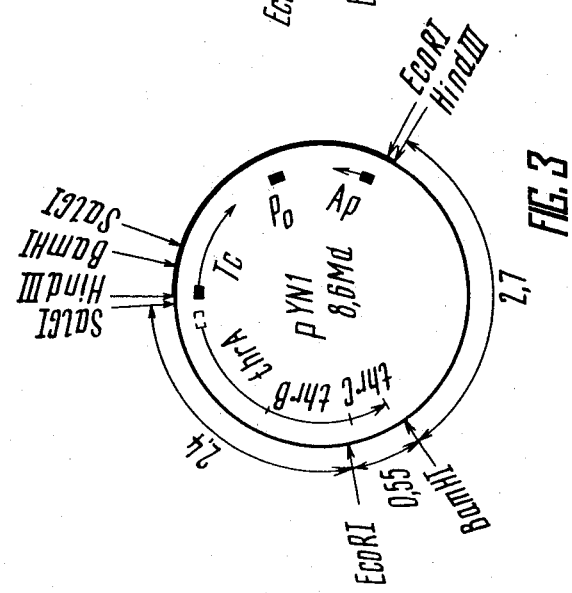

Using the same donor strain and plasmid pBR322 as the vector, but employing the specific endonuclease Hind III, the hybrid plasmid pYNll is obtained which contains all three genes of threonine operon. The accompanying drawing also represents the restrictional chart of the plasmid pYNll (FIG. 3). The reference characters are the same as in FIG. 1.

Transformation of the recipient strain *E. coli* VL334 with the resulting hybrid plasmide caused an increased output of threonine: during fermentation in the culture liquid there accumulated up to 4 g/l of the aminoacid. In this manner it has been found that in order to increase productivity with respect to threonine, it is necessary to amplify all three genes of threonine operon. Furthermore, the experiments carried out by the inventors have made it possible to choose the endonuclease Hind III for the preparation of a fragment of the chromosome of *E. coli* containing all genes of threonine operon. The determination of specific activity of homoserinedehydrogenase I (product of gene thrA) in extracts from cells of the strain *E. coli* VL334 (pYNll) has shown it is more than 60 times higher than the specific activity of the same enzyme in extracts from cells containing only one copy of the gene thrA. At the same time, as to the level of production of threonine, the strain *E. coli* VNIIGenetika VL334 (pYNll) bearing the hybrid plasmid with the wild-type threonine operon only insignificantly surpasses the plasmidless strain *E. coli* VNIIGenetika MG442 having a mutation in the gene thrA which breaks allosterical inhibition of enzyme products of this gene by threonine. It has been assumed that this low level of the synthesis of threonine by cells of the strain *E. coli* VL334 (pYN11) is associated with the fact that the accumulating threonine suppresses activity of the enzymes controlling the synthesis of threonine and, in particular, homoserinedehydrogenase I. In this respect, it is deemed to be expedient to use, as the donor strain for cloning of the threonine operon, the strain *E. coli* VNIIGenetika MG 442 with broken negative regulation of the synthesis of threonine. Using the strain *E. coli* VNIIGenetika MG442 as the donor and the plasmide pBR322 as the vector, as well as employing the endonuclease Hind III for the preparation of DNA fragments, the hybrid plasmid pYN10 has been constructed. Its restrictional map does not differ from the chart of pYN11 shown in FIG. 3. After transformation, with the plasmid pYN10, of the recipient strain *E. coli* VL334, the strain *E. coli* VL334 (pYN10) has been obtained which produces 12-13 g/l of threonine.

Consequently, for the preparation of the strain producing an aminoacid by means of hybride plasmids, it is required that a mutation be present on the cloned fragment which mutation damages the negative regulation of the synthesis of the aminoacid.

In experiments with hybrid plasmids of a different molecular weight it has been found, in correspondence with the known data, that the number of copies of hybrid plasmids as calculated for a bacterial chromosome varies from 10 to 22 and depends on their sizes. The lower the molecular weight of the plasmid, the greater number of its copies is contained in a cell. On the other hand, activity of enzymes controlled by the genes positioned on the plasmid is increased proportionally to the number of copies of the plasmid. In this respect, it is advisable to diminish the size of the hybrid plasmid bearing the genes which control the synthesis of the predetermined aminoacid by eliminating the ballast genetic material.

Determining activity of homoserinedehydrogenase I in extracts from cells carrying hybrid plasmids has shown that high concentrations (1 mg/ml) of threonine and isoleucine in the medium suppress activity of this enzyme by 3-4 times. This fact is considered a manifestation of repression of the amplified threonine operon. Therefore, it is advisable to create the conditions of derepression for the maximum manifestation of the amplified threonine operon.

In the recipient strain the conditions of derepression may be created by damaging the controlling gene monitoring the synthesis of the depressor protein, or by deteriorating the synthesis of the repression cofactor. In particular, derepression of the threonine operon may be accomplished by the introduction, into the recipient strain, of a mutation breaking the synthesis of isoleucine which takes part in repression of the threonine operon. It has been found that in the presence of the mutation ilvA partly blocking the synthesis of isoleucine in the recipient strain VL334, the synthesis of threonine, controlled by the hybrid plasmid, is increased by 4-5 times.

As it has been shown earlier, the strain Vl334, wherein the synthesis of threonine is blocked as a result of mutation of thrC, and the related step of threonine metabolism, i.e. its transformation to isoleucine, is blocked partly due to the ilvA mutation, is also capable of growing on a medium with a high concentration of threonine in the absence of isoleucine. It is obvious that the cells with hybrid plasmids capable of producing considerable amounts of threonine will also be capable of being grown on a medium without isoleucine. Indeed, after transforming the strain VL334 by hybrid plasmids bearing all three genes of the threonine operon, the cells are capable of being grown on a glucose-mineral medium containing no additional growth factors.

The cells containing hybrid plasmids with the complete threonine operon under non-selective conditions easily lose the hybrid plasmid and cleave the starting recipient strain which is auxotrophic with respect to threonine ad isoleucine. However, when grown on a minimal medium containing no additonal growth factors, the cells bearing the hybrid plasmid have a selective advantage over the cells having lost the plasmid. Under these conditions they synthesize a considerable amount of threonine which is taken up into the medium. Threonine accumulated in the medium may stimulate the growth of cells having lost the hybrid plasmid.

However, it is only at a concentration of threonine within the range of from 10 to 15 g/l, that the growth rate of plasmidless cells of the strain VL334 approaches the growth rate of the cells carrying the hybrid plasmid containing the complete threonine operon from the donor strain *E. coli* VNII Genetika MG442. Therefore, the mutation partly blocking the related step of metabolism of the given aminoacid ensures a stable development of the population of cells bearing the hybrid plasmid with the genes controlling the synthesis of the given aminoacid under fermentation conditions.

The method for preparing strains producing aminoacids according to the present invention makes it possible, by using genetic engineering techniques directed to increasing the dose of genes required for biosynthesis of the needed aminoacid, to produce strains necessitating no additional growth factors and possessing an increased capability of producing the required aminoacid.

For a better understanding of the present invention the following specific Examples illustrating the method for preparing the strains which produce aminoacids are given hereinbelow.

EXAMPLE 1

As the donor strain use in made of *E. coli* VNIIGenetika MG 442. The strain is resistant with respect to the analogue of threonine ($\beta$-hydroxynorvaline) and contains a mutation in the gene thrA, destroying the allosterical inhibition of activity of homoserinedehydrogenase I (the key enzyme in the biosynthesis of threonine) by threonine. As the vector molecule of DNA use is made of the plasmid pBR322. This plasmid is created on the basis of the replicon ColEI and contains genes of resistance to ampicillin/penicillin (Ap$^r$) and tetracycline (Tc$^r$). The fragment of DNA chromosome of the donor strain *E. coli* VNIIGenetika MG442 and the plasmid pBR322 are isolated by conventional methods. For the construction of hybrid plasmids, the chromosome fragment of DNA of the donor strain and the plasmid pBR322 are treated with the endonuclease Hind III for 1.5 hour at a temperature of 37° C., heated for 10 minutes at a temperature of 65° C. and the joining is effected by means of polynucleotide ligase of the phage T4 for a period of 18 hours at a temperature of 6° C. The resulting mixture is used for transformation of cells of the strain C600 thr$^-$ leu$^-$. The transformants are selected on the medium with 500 mcg/ml of penicillin and 50 mcg/ml of leucine. Bacteria of two phenotypic classes Ap$^r$Tc$^s$Thr$^+$Leu$^-$ and Ap$^r$Tc$^r$Thr$^+$Leu$^-$ are obtained. For the separation and analysis of the extrachromosomal DNA, one clone of transformants of every class is arbitrarily selected. From the transformants of the first class with the phenotype Ap$^r$Tc$^s$Thr$^+$Leu$^-$ a hybrid plasmid pY-N10 is recovered containing a fragment of the plasmid pBR322 and a fragment of the donor chromosome with the weight of 5.8 Megadalton. The strain E. coli mutations is various genes of the threonine operon is transformed by means of the resulting plasmid to verify the presence and functioning therein of all three genes of threonine operon. The resulting hybrid plasmid is used to transform the strain E. coli with mutations in the following genes of the threonine operon: Gt 14 (thrA$_1^-$), Gif 102 (thrA$_2^-$), Gt 25 (thrB$^-$), VL334 (thr C$^-$). In all cases the transformed bacteria become prototrophic with respect to threonine which demonstrates the presence, on the plasmid, of all three genes of threonine operon (thrA, thrB and thrC). The insertion of the chromosome fragment DNA into the plasmid pBR322 cleaved by the endonuclease Hind III results in the inactivation of the plasmid genes defining resistance against tetracycline, since the site of cleaving by this endonuclease is in the promotor of these genes which is shown in FIG. 1. From the bacteria of the second phenotypic class Ap$^r$Tc$^r$Thr$^+$Leu$^-$ the plasmid with the molecular weight of 11.4 megadalton is recovered. The restrictional analysis of this plasmid denoted as pYN6 shows that it consists of a chromosome Hind III-fragment of DNA (with the molecular weight of 5.8 megadalton) and two copies of the plasmid pBR322 connected "head"-to-"tail" which is shown in FIG. 4, wherein the restrictional map of the plasmid pYN6 is represented. Dotted arcs show the fragments of the plasmid, wherefrom the plasmid pYN7 is formed. The other reference characters are the same as in FIG. 1. The cleavage of the plasmid pBR322 by the endonuclease Hind III results in cleaving the promotor of the genes defining resistance against tetracycline. A successive connection of the resulting fragments in one of two possible orientations results in the exact restoration of the promotor structure and functioning of the genes defining resistance against tetracycline. For this reason, the cells containing the plasmid pYN6 are resistant against this antibiotic. Transformation with the plasmid pYN6, of the strains E. coli containing mutations in different genes of the threonine operon shows that in this plasmid there are present and functioning all three genes of threonine operon. To prepare the strain producing threonine, use is made of the resulting hybrid plasmid pYN6 which is used to effect transformation of the recipient strain E. coli VL334 bearing the mutation thrC 1010 and ilvA 442. The mutation thrC 1010 breaks the synthesis of threonine, thus making it possible to select the transformants acquired by the hybrid plasmid. The mutation ilvA 442 partly blocks the related step of threonine metabolism, i.e. the first reaction in the route of conversion of threonine to isoleucine and thus destroys the conversion of threonine and synthesis of isoleucine which participates in repressing the threonine operon.

Blocking the synthesis of isoleucine is not complete and may be compensated by an increased content of threonine in a cell.

The transformants acquired by the plasmid pYN6 are selected on a medium containing 500 mcg/ml of penicillin and 20 mcg/ml of tetracycline, but containing no threonine and isoleucine. The resulting strain is denoted as E. coli VNIIGenetica VL334 (pYN6). It is resistant against penicillin and tetracycline and capable of growing on a medium without aminoacids. The ability of growing without isoleucine is associated with a high level of threonine in cells of the strain E. coli VNIIGenetika VL334 (pYN6) which is ensured by amplification of the mutant threonine operon thus imparting a selective advantage to the cells carrying the hybrid plasmid over the cells having lost it. The resulting strain E. coli VNIIGenetika VL334 (pYN6) contains about 10 copies of the plasmid pYN6 as calculated per chromosome. The results of the production tests of the resulting strain are given in Example 3.

EXAMPLE 2

Figure 5:
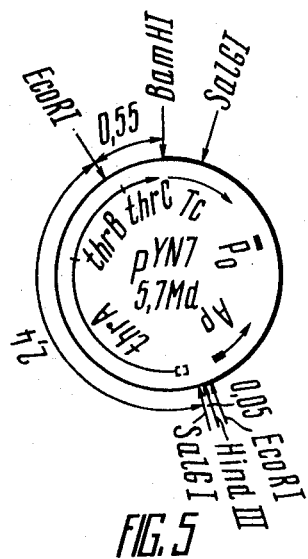

The plasmid pYN6 or pYN10 prepared by the method similar to that described in Example 1 is treated with specific endonucleases Hind III and Bam HI. After inactivation of the enzymes by heating at a temperature of 65° C. for 10 minutes, the mixture is treated with the polynucleotide ligase of phage T4. The resulting preparation is used for transformation of bacteria of the strain C600 and clones with the phenotype Ap$^r$Tc$^s$Thr$^+$ are selected. The plasmid with the molecular weight of 5.7 megadaltons denoted pYN7 is isolated from one arbitrarily chosen clone. As has been shown by the restrictional analysis, upon cleaving this plasmide with endonucleases Hind III and Bam HI two fragments are formed, one of which corresponds to the greater portion of the plasmid pBR322 (2.7 Md) and the other comprises a fragment of DNA chromosome of the strain VNIIGenetika MG442 (3.0 Md) which is shown in FIG. 5. In the schematic diagram of the plasmid pYN6 these fragments are shown by dotted arcs (see FIG. 4). Transformation, with the plasmid pYN7, of the strains with mutations in different genes of the threonine operon shows that in this plasmid all three genes of the threonine operon are functioning.

To prepare the strain producing threonine, the plasmid pYN7 is used for transformation of the strain E. coli VL334 bearing mutations in the gene thrC and ilVA. The transformants acquired by the plasmid pYN7 is selected on the medium containing 500 mcg/ml of penicillin, but without threonine and isoleucine. The resulting strain is called E. coli VNIIGenetika VL334 (pYN7). It is resistant against penicillin and capable of growing on a medium without aminoacids.

In cells of the resulting strain VNIIGenetika VL334 (pYN7) there are about 20 copies of the plasmid pYN7 as calculated per chromosome. The results of productivity of the thus-prepared strain are given in Example 3.

EXAMPLE 3

The strains prepared by the method according to the present invention described in Examples 1 and 2 hereinbefore, i.e. strain E. coli VNIIGenetika VL334 (pYN6), strain E. coli VNIIGenetika VL334 (pYN7) and strain E. coli VNIIGenetika MG 442 (for the purpose of comparison) are inoculated by loop from the slant of an agarized Adams medium containing 0.5 mg/ml of a potassium salt of benzylpenicillin into conically-shaped flasks with a capacity of 250 ml each containing 30 ml of a liquid Adams medium (glucose 1%). After inoculation, the flasks are placed on a circular shaker (200 r.p.m.) and incubated for 18 hours at the temperature of 37° C. The thus cultured inoculation material is used in an amount of 1 ml for inoculation of a preliminarily sterilized (by the method described hereinbelow) fermentation medium added by portions of 15 ml to cone-shaped 250 ml flasks.

The fermentation media have the following composition:

|  | Medium 1 | Medium 2 | Medium 3 |
|---|---|---|---|
| Glucose | 30 | 50 | 80 |
| $(NH_4)_2SO_4$ | 10 | 15 | 20 |
| $KH_2PO_4$ | 2 | 2 | 2 |
| $MgSO_4$ | 1 | 1 | 1 |
| $CaCO_3$ | 20 | 20 | 30 |

The fermentation media are sterilized in an autoclave under an excess pressure of 0.5 atm for 15 minutes. Chalk is sterilized separately and introduced into the medium after sterilization. After the addition of chalk the medium has a pH within the range of from 6.8 to 7.2.

The flasks containing said media are placed, after inoculation with the cultures of the above-mentioned strains, onto a circular shaker (220 r.p.m.) and incubated for a period of 48 hours at a temperature of 37° C. 95% of the cells after fermentation retain the capability of growing without threonine and isoleucine and are resistant against amplicillin which proves the presence of plasmids in cells of these strains.

The amount of threonine formed by the strains is shown in Table 1 hereinbelow.

In the case of production of L-threonine in a fermenter, the inoculation material of the strain *E. coli* VNIIGenetika VL334(pYN7) prepared as described in Example 2 in the amount of 25 ml is introduced into a laboratory fermenter, whereinto 250 ml of the fermentation medium No. 1 have been preliminary charged. The fermentation conditions are as follows: temperature 37° C., the amount of air supplied to the apparatus 1.1 (by the flow meter), stirrer speed 900 r.p.m. 28 hours after the beginning of the fermentation, the supply of the feeding material comprising a 10-fold concentrate of the fermentation medium No. 1 without chalk is started. The feeding is effected by means of a peristaltic pump at the rate of 1.5 ml/hr. 51 hours after the beginning of the fermentation threonine is accumulated in the medium in an amount of 20 g/l. 95% of cells after fermentation contain the plasmid pYN7. The test results are shown in Table 1 hereinbelow.

TABLE 1

| Strain | Plasmid in the strain | Fermentation medium No. | Accumulation of threonine, g/l |
|---|---|---|---|
| *E. coli* VNIIGenetika MG442 | no plasmid | 1 | 3.0 |
|  |  | 2 | 3.3 |
|  |  | 3 | — |
| *E. coli* VNIIGenetika VL334(pYN6) | plasmid pYN6 | 1 | 7.0 |
|  |  | 2 | 11.2 |
|  |  | 3 | 14.4 |
| *E. coli* VNIIGenetika VL334(pYN7) | plasmid pYN7 | 1 | 20.0* |
|  |  | 2 | 13.3 |
|  |  | 3 | 16.5 |

*In a fermenter with feeding of the nutrient medium.

l-threonine is recovered from the culture liquid by conventional methods.

As follows from the above Table 1, the highest level of production of the aminoacid is characteristic for the strains containing a hybrid plasmid.

What is claimed is:

1. A method for preparing bacterial strains which produce aminoacids comprising combining a chromosome DNA fragment of a donor bacterium containing genes controlling the synthesis of a selected aminoacid and having a mutation which destroys the negative regulation of the synthesis of said aminoacid, with a plasmid DNA molecule capable of ensuring amplification, to form a hybrid DNA molecule; transforming with said hybrid DNA molecule, cells of a recipient bacterial strain having a mutation blocking the synthesis of the selected aminoacid in said strain and a mutation partly blocking the related step of metabolism of said aminoacid, to yield a bacterial strain possessing increased productivity of the selected aminoacid.

2. A method as claimed in claim 1, wherein for the removal of ballast genetic material, the hybrid DNA molecule is treated, prior to transforming cells of the recipient strain, with specific endonucleases ensuring cleavage of the hybrid molecule of DNA in predetermined sites of the molecule, followed by recombination and joining of the required DNA fragments with polynucleotide ligase.

3. A method as claimed in claim 1 for preparing a strain which produces L-threonine, wherein a fragment of the chromosome DNA of the donor strain *E. coli* VNIIGenetika MG442, produced by means of the endonuclease Hind III containing genes of threonine operon which as a result of mutation is insensitive to inhibition by threonine is combined witb plasmid pBR322 to form a hybrid plasmid having a molecular weight of 11.4 Megadaltons, consisting of two copies of the plasmid pBR322 and said chromosome DNA fragment of the donor strain; said hybrid plasmid transforming cells of the recipient strain *E. coli* VL334 having mutations blocking the synthesis of L-threonine and L-isoleucine, the blocking with respect to isoleucine being partial; wherein the strain *E. coli* VNIIGenetika VL334 (pYN6) which produces L-threonine is obtained and identified by registration number CMIM B-1649.

4. A method as claimed in any of claims 1 or 2 for preparing a strain which produces L-threonine, wherein a fragment of the chromosome DNA of the donor strain *E. coli* VNIIGenetika MG442, produced by means of the endonuclease Hind III containing genes of threonine operon which as a result of mutation is insensitive to inhibition by threonine is combined with plasmid pBR322 to form a hybrid plasmid with a molecular weight of 11.4 Megadaltons, consisting of two copies of the plasmid pBR322 and said fragment chromosome DNA of the donor strain; said hybrid plasmid being treated with endonucleases Hind III and Bam HI and the obtained fragments recombined and joined by treating same with polynucleotide ligase; said treated hybrid plasmid having a molecular weight of 5.8 Megadaltons, and consisting of one molecule of the plasmid pBR322 and said chromosome DNA fragments of the donor strain, ensuring resistance of the resulting cells against penicillin and may be contained in cells at the stage of logarithmic growth in an amount of about 20 copies; transforming with said treated hybrid plasmid, cells of the recipient strain *E. coli* VL334 having mutations blocking the synthesis of L-threonine and L-isoleucine, the blocking of isoleucine synthesis being partial; wherein the strain *E. coli* VNIIGenetika VL334 (pYN7) which produces L-threonine is obtained and identified by the registration number CMIN B-1684.

* * * * *